(12) United States Patent
Shintou

(10) Patent No.: US 6,603,007 B1
(45) Date of Patent: Aug. 5, 2003

(54) BIPYRIDYL DERIVATIVES

(75) Inventor: Taichi Shintou, Hiratsuka (JP)

(73) Assignee: Sankio Chemical Co., Ltd., Tokyo (JP)

(*) Notice: Subject to any disclaimer, the term of this patent is extended or adjusted under 35 U.S.C. 154(b) by 0 days.

(21) Appl. No.: 10/130,068

(22) PCT Filed: Oct. 30, 2000

(86) PCT No.: PCT/JP00/07628

§ 371 (c)(1),
(2), (4) Date: May 15, 2002

(87) PCT Pub. No.: WO01/36387

PCT Pub. Date: May 25, 2001

(30) Foreign Application Priority Data

Nov. 15, 1999 (JP) ............................................. 11-324451

(51) Int. Cl.$^7$ ............................................. C07D 213/22
(52) U.S. Cl. ...................................................... 546/257
(58) Field of Search ......................................... 546/257

(56) References Cited

FOREIGN PATENT DOCUMENTS

| GB | 2 328 686 A | 3/1999 |
|---|---|---|
| WO | WO 92/02513 * | 2/1992 .......... C07D/253/65 |
| WO | WO 98/52922 | 11/1998 |

OTHER PUBLICATIONS

Prostakov et al, Chemical Abstracts, vol. 106, No. 21, Abstract 176,128u, p. 704, May 25, 1987.*

Katsuyoshi Yamakawa, et al., Synthesis of Cyan Dye–forming Coupler for Color Photographic Use, 1998, pp. 78–86, Journal of Synthetic Organic Chemistry, Japan 56 (9).

Paola Ceroni et all., Dinuclear and Dendritic Polynuclear Ruthenium (II) an dOsmium (II) Polypyridine Complexes: Electrochemistry at Very Positive Potentials in Liquid $SO_2$, J. Am. Chem. Soc., 120, 1998, pp. 5480–5547.

* cited by examiner

*Primary Examiner*—Zinna Northington Davis
(74) *Attorney, Agent, or Firm*—Sughrue Mion, PLLC

(57) ABSTRACT

Provided are novel specific dipyridyl derivatives as a useful substance or an intermediate in the fields of pharmaceuticals, agrichemicals, ligands, silver halide photosensitive materials, liquid crystals, surfactants, electrophotography and organic electroluminescence.

7 Claims, No Drawings

BIPYRIDYL DERIVATIVES

This application is a 371 of PCT/JP00/07628 filed Oct. 30, 2000.

TECHNICAL FIELD

The present invention relates to novel dipyridyl derivatives serving as an important intermediate in the fields of pharmaceuticals, agrichemicals, ligands, silver halide photosensitive materials, liquid crystals, surfactants, electrophotography and organic electroluminescence.

BACKGROUND ART

In recent years, pyridine derivatives have attracted attentions in a wide range of fields. In the fields of pharmaceuticals and agrichemicals, pyridine derivatives exhibit, as an endothelin antagonist, have high affinity for endothelin receptors (Japanese Patent Laid-Open No. Hei 9-162449, Japanese Patent Laid-Open No. Hei 10-194972, Japanese Patent Laid-Open No. Hei 11-92458). The affinity for the receptors are however insufficient and there is a strong demand for the creation of endothelin antagonists having more potent affinity for the receptor. As pharmaceuticals having a cerebral nerve protecting action such as remedies for aftereffects of cerebral infarction, compounds having, as a basic skeleton, a dipyridyl skeleton in its chemical structure have been researched and developed briskly. For example, in WO9852922, such a compound is disclosed.

In the fields of ligands, the research of dendrimer-type polynuclear metal complexes contained in dendrimer type compounds has proceeded at a brisk pace, because they exhibit new properties as the polynuclear metal complex when the mutual action between subunits is strong. As one of the studies, a polynuclear complex (Chemistry and Chemical Industry, 52(7), 890(1999), J. Am. Chem. Soc., 120, 5480(1998)) is synthesized, and the polynuclear complex is used a photo- and redox-active ruthenium (II) polypyridine complex as a sub-unit and as a bridging ligand, a pyrazine having an electron mutual action between skeletons, and its electrochemical properties are reported. There is a possibility of such a dendrimer-type polynuclear metal complex being used for artificial conversion process of solar energy and it is expected much as a promising substance.

Usefulness of the pyridine derivatives as a ligand of various reaction catalysts is also expected. For example, as described in GB2328686 or Journal of Synthetic Organic Chemistry, Japan, 56(9), 78(1998), they are expected to serve as a reactive accelerator when used as a ligand of a metal copper catalyst in the Ullmann type reaction.

In the fields of silver halide photosensitive materials, pyridine derivatives and various pyridinium compounds obtained by quaternizing these derivatives have been widely used as a nucleating development accelerator or crystal habit modifier. They are disclosed, for example, in Japanese Patent Laid-Open No. Hei 6-242534 or Japanese Patent Laid-Open No. Hei 8-227117.

In the field of liquid crystals, since incorporation of a pyridine derivative in the molecular structure of a liquid-crystal compound makes it possible for the resulting compound to exhibit various excellent properties of liquid crystal, studies on it have been made briskly. For example, such a study is disclosed, for example, in Japanese Patent Laid-Open No. Hei 8-295884, Japanese Patent Laid-Open No. Hei 9-25567, Japanese Patent Laid-Open No. Hei 9-110856, Japanese Patent Laid-Open No. Hei 10-7596 or Japanese Patent Laid-Open No. Hei 10-237002.

In the field of organic electroluminescence (EL) attracting attentions as a next-generation display material, absence of effective electron transporting materials has come to be a problem (for electron transporting materials, introduction of π electron system having high electron acceptance is indispensable). It has recently been reported that silole derivatives (silole (silacyclopentadiene) is a silicon homologue of cyclopentadiene) whose lowest unoccupied molecular orbit (LUMO) is low and electron acceptance is high, particularly 2,5-dipyridylsilole having as an aryl group a 2-pyridyl group has markedly high electron transporting properties and these electron transporting properties are superior to those of tris(8-hydroxyquinoline)aluminum Alq which has been regarded as one of the best electron transporting materials (Journal of Synthetic Organic Chemistry, Japan, 56(6), 50(1998), J. Am. Chem. Soc., 118, 11974 (1996)). In the molecular design of the silole π electron system, particularly, a 2,5-diarylsilole derivative, how to control its electron structure and physical properties (for example, control by the substituent on the 2,5-aryl group) has drawn attentions.

In the field of electrophotography, the pyridine derivatives are used as a portion of the pigment of recording materials as disclosed, for example, in Japanese Patent Laid-Open No. Hei 3-282478 or Japanese Patent Laid-Open No. Hei 10-265690. Since they have a substituent permitting formation of two conformations in the pigment, they are used for the purpose of improving image stability, particularly, fixing property or light resistance. Pyridine derivatives are thus briskly studied also in this field. With a recent rapid increase in the amount of information, optical storage media of a large capacity have been highlighted. This field is therefore regarded promising as an application field of pyridine derivatives.

An object of the present invention is to provide novel dipyridyl derivatives which are useful substances or intermediates in the fields of pharmaceuticals, agrichemicals, ligands, silver halide photosensitive materials, liquid crystals, surfactants, electrophotography and organic electroluminescence.

DISCLOSURE OF THE INVENTION

As a result of extensive investigation, the present inventors have succeeded in obtaining novel dipyridyl derivatives useful in the fields of pharmaceuticals, agrichemicals, ligands, silver halide photosensitive materials, liquid crystals, surfactants, electrophotography and organic electroluminescence and completed the following inventions.

(1) A dipyridyl derivative represented by the following formula (A):

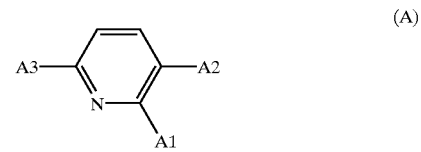

wherein A1 and A2 may be the same or different and each represents an alkyl or aryl group; A1 and A2 may be coupled together to form a ring; and A3 represents one of the following structures:

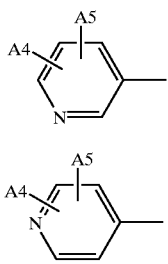

(AI)

(AII)

wherein A4 and A5 may be the same or different and each represents a hydrogen atom, an alkyl group or an aryl group.

(2) The dipyridyl derivative according to the above (1), wherein in A1, A2, A4 or A5 of the formula (A), the alkyl group has 1 to 4 carbon atoms and the aryl group is a phenyl or naphthyl group.

(3) The dipyridyl derivative according to the above (2), wherein in the formula (A), A1 and A2 are the same.

(4) A dipyridyl derivative represented by the following formula (B):

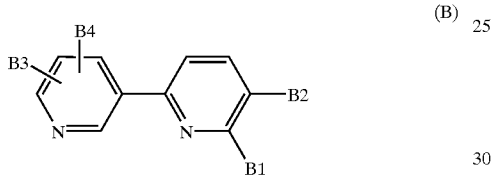

(B)

wherein one of B1 and B2 represents a hydrogen atom, and the other represents an alkyl or aryl group, and B3 and B4 may be the same or different and each represents a hydrogen atom, an alkyl group or an aryl group, with the proviso that when B3 and B4 simultaneously represent a hydrogen atom, the following cases are excluded:
(i) one of B1 and B2 represents an alkyl group having 3 or less carbon atoms, and
(ii) B1 represents a phenyl group, and with the further proviso that when B2 represents a hydrogen atom, the following case are excluded:
(i) each of B1 and B3 (substituted at the 6-position) represents a phenyl group and B4 represents a hydrogen atom, or
(ii) B1, B3 (substituted at the 2-position) and B4 (substituted at the 6-position) each represents a methyl group.

(5) The dipyridyl derivative according to the above (4), wherein in B1, B2, B3 or B4 of the formula (B), the alkyl group has 1 to 4 carbon atoms and the aryl group is a phenyl or naphthyl group.

(6) A dipyridyl derivative represented by the following formula (C):

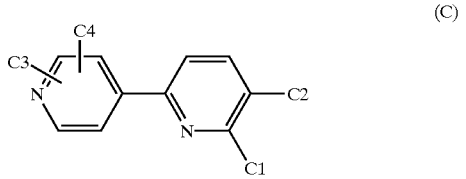

(C)

wherein one of C1 and C2 represents a hydrogen atom and the other one represents an alkyl or aryl group; and C3 and C4 may be the same or different and each represents a hydrogen atom, an alkyl group or an aryl group, with the proviso that when C3 and C4 simultaneously represent a hydrogen atom, C1 or C2 does not represent a methyl group.

(7) The dipyridyl derivative according to the above (6), wherein in C1, C2, C3 or C4 of the formula (C), the alkyl group has 1 to 4 carbon atoms and the aryl group is a phenyl or naphthyl group.

(8) A dipyridyl derivative represented by the following formula (D):

(D)

wherein D1 represents one of the following structures:

(DI)

(DII)

wherein D2 represents an alkyl or aryl group; and D3 represents a hydrogen atom, an alkyl group or an aryl group, with the proviso that when D1 represents the formula (DI), the following cases are excluded:
(i) one of D2 and D3 is a methyl group substituted at the 5-position, and the other one is a methyl or phenyl group substituted at the 6-position, and
(ii) D2 represents a phenyl group substituted at the 2-position and D3 represents a hydrogen atom, and
with the further proviso that when D1 represents the formula (DII), the following cases are excluded:
(i) D2 represents a methyl group substituted at the 3-position and D3 represents a hydrogen atom,
(ii) one of D2 and D3 is a methyl group substituted at the 2-position and the other one is a methyl group substituted at the 6-position, and
(iii) one of D2 and D3 is a methyl group substituted at the 2- or 3-position and the other one is a phenyl group substituted at the 6-position.

(9) The dipyridyl derivative according to the above (8), wherein in D2 or D3 of the formula (D), the alkyl group has 1 to 4 carbon atoms and the aryl group is a phenyl or naphthyl group.

Invention compounds will next be described more specifically.

In this specification, examples of the alkyl group include linear or branched alkyl groups having 1 to 18 carbon atoms, preferably alkyl groups having 1 to 4 carbon atoms such as methyl, ethyl, propyl, isopropyl, butyl, isobutyl, sec-butyl and tert-butyl, more preferably methyl and ethyl groups which can be introduced into carboxylic acid or aldehyde.

In this specification, the aryl group may be substituted. Specific examples include phenyl, tolyl, naphthyl, hydroxyphenyl and dimethylaminophenyl, of which phenyl, tolyl and naphthyl groups are preferred, with phenyl and naphthyl groups being more preferred.

In the above-described substituent, A1 and A2 may be the same or different, but it is preferred that A1 and A2 are the same.

Alternatively, A1 and A2 may be coupled together to form a ring. Specific examples of the ring formed by them include cycloalkanes such as cyclopentane, cyclohexane, cycloheptane and cyclooctane, with cyclohexane being preferred.

Specific examples (I-1) to (I-70) of the invention compounds represented by any one of the formulas (A) to (D) will next be described, but the present invention is not limited to them.

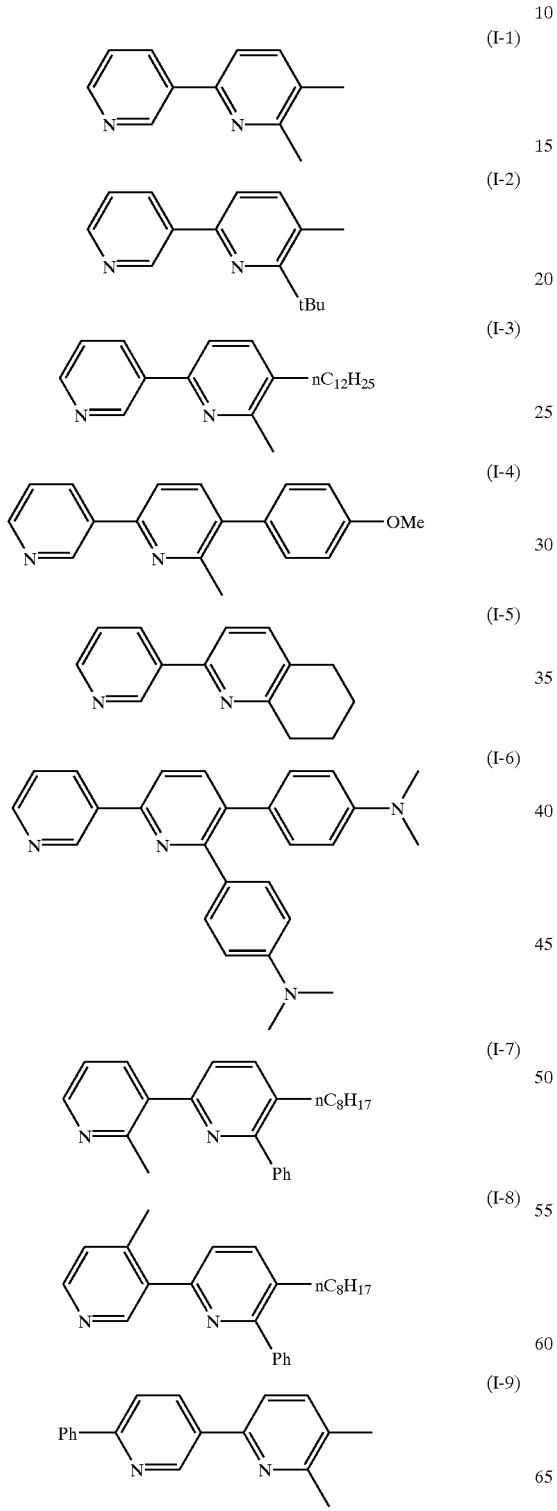

-continued

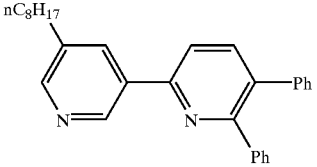
(I-10)

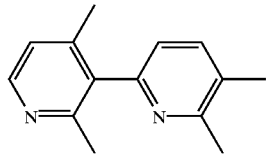
(I-11)

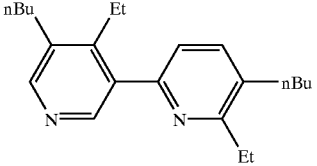
(I-12)

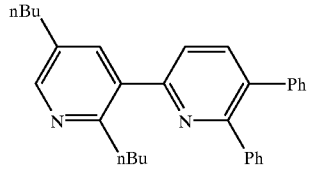
(I-13)

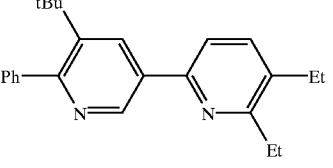
(I-14)

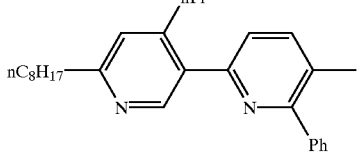
(I-15)

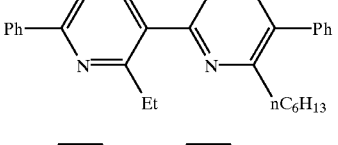
(I-16)

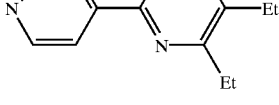
(I-17)

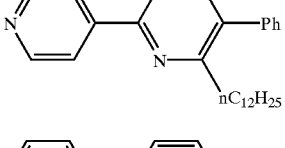
(I-18)

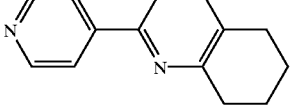
(I-19)

-continued
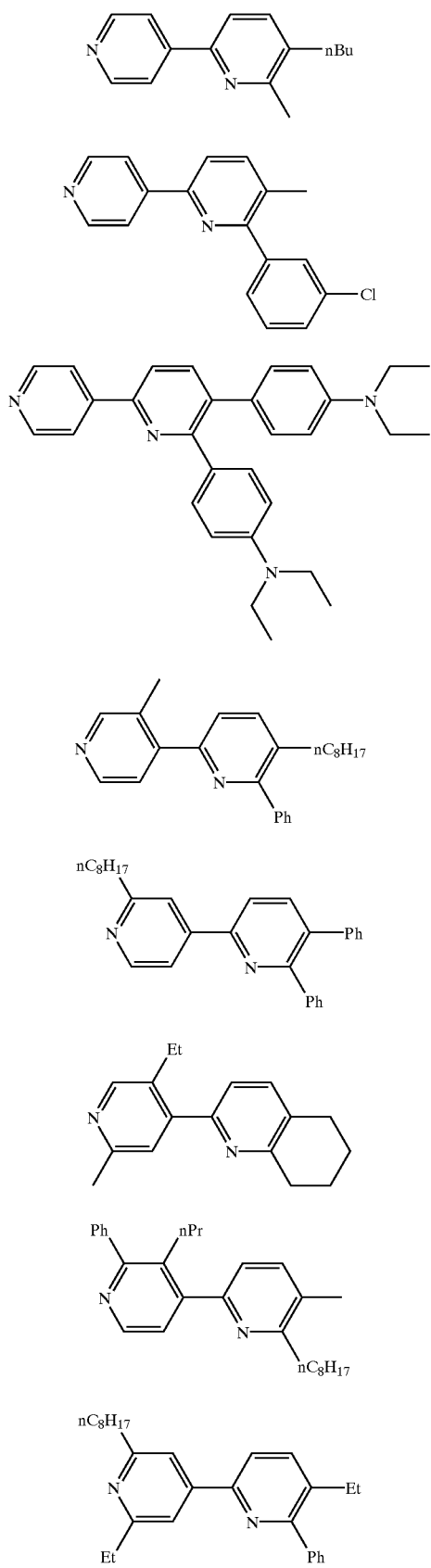
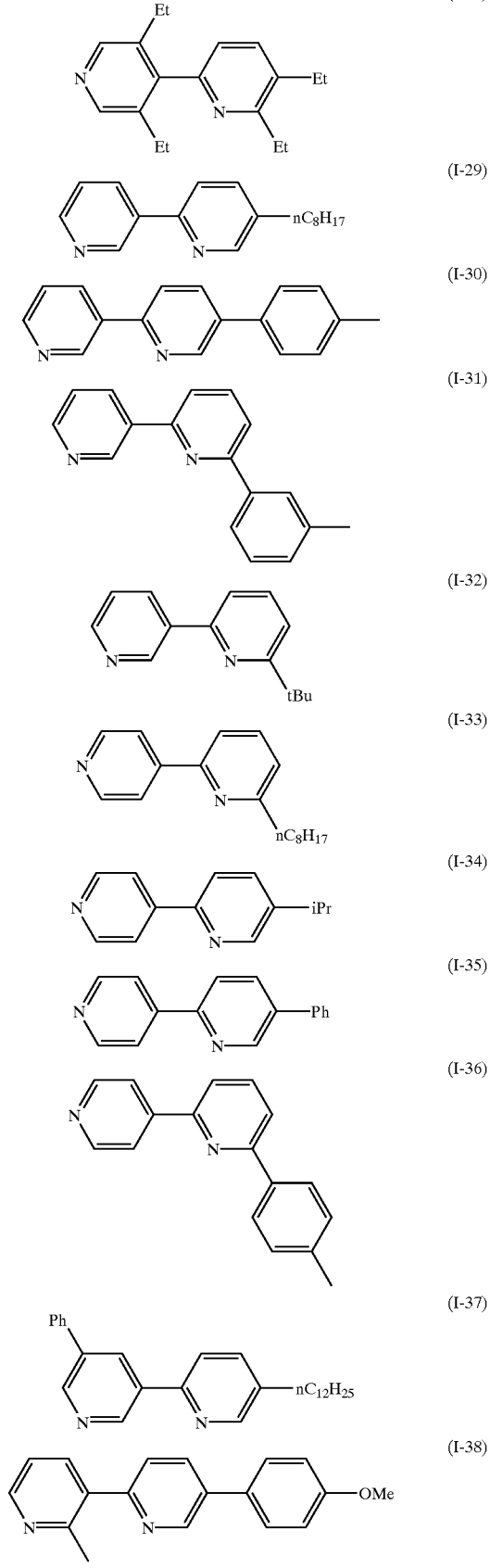

-continued
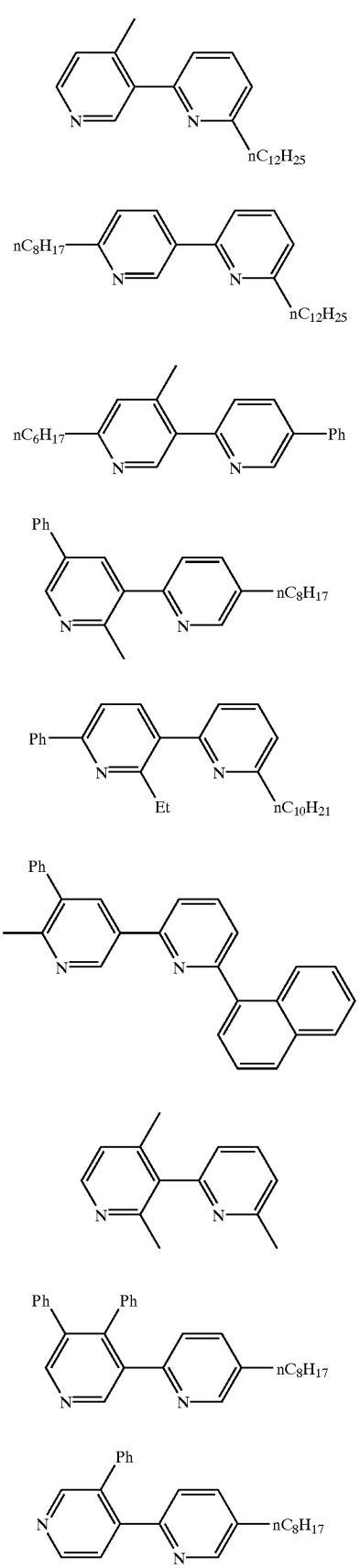
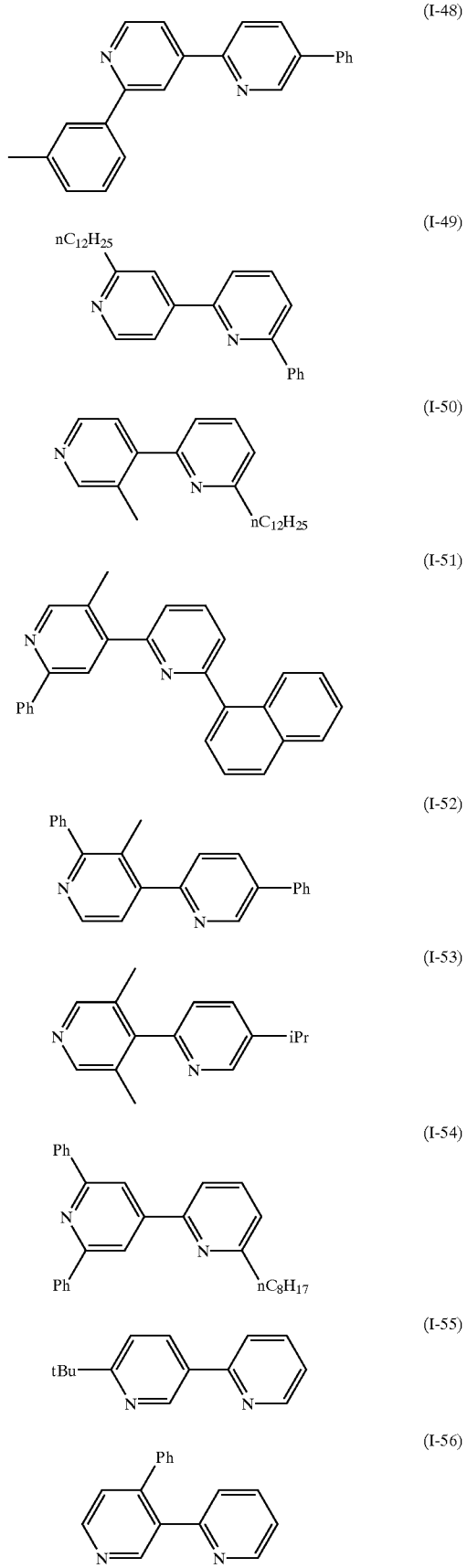

(I-57) 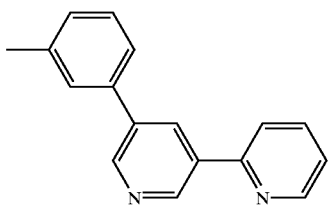
(I-58) 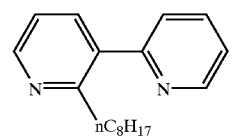
(I-59) 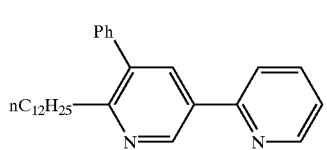
(I-60) 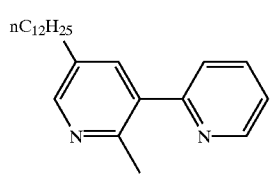
(I-61) 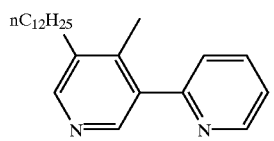
(I-62) 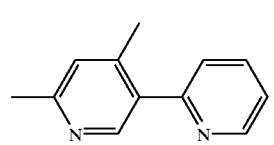
(I-63) 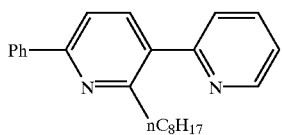
(I-64) 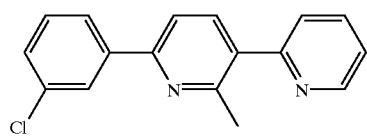
(I-65) 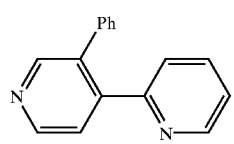
(I-66) 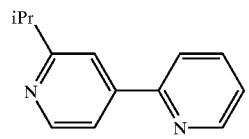
(I-67) 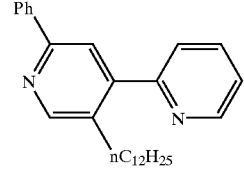
(I-68) 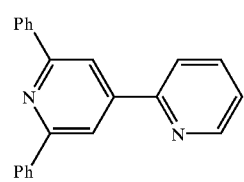
(I-69) 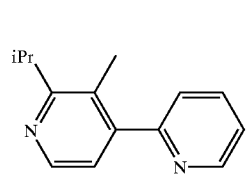
(I-70) 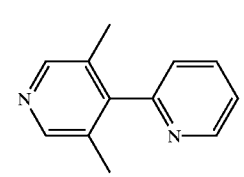
One example of a preparation process of the dipyridyl derivatives of the present invention represented by the formulas (A) to (D) will next be described.
It should however be noted that the details of present invention are not limited thereto.
Preparation Process
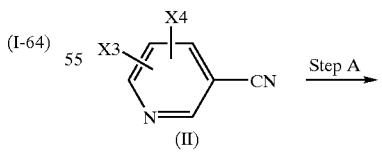
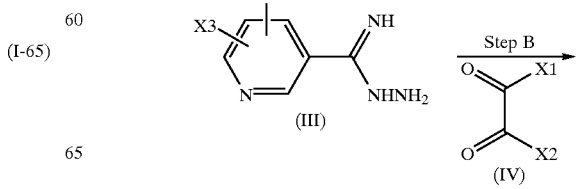

-continued

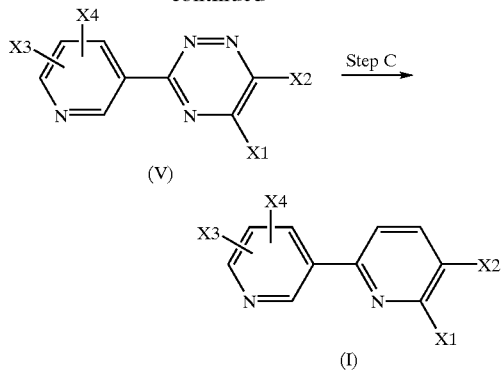

In the above-described reaction scheme, X1 to X4 represent substituents corresponding to those in the above-described formulas (A) to (D) of the present invention.

The other invention compounds can be prepared as described in the above.

A description will next be made of each step.

Step A

An amidrazone compound of the formula (III) is obtained by reacting a cyanoheterocyclic compound of the formula (II) with a hydrazine. The amidrazone compound (III) is available by the process as described in Japanese Patent Application Hei 11-167308 or by the process in accordance therewith.

Specific examples of the cyanoheterocyclic compound usable in the present invention include those represented by the following formulas (II-1) and (II-2).

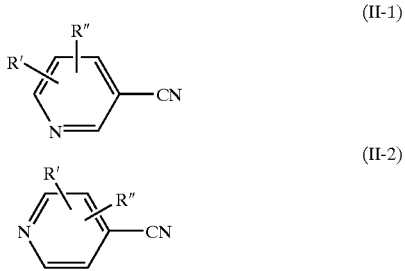

In the above-described formulas, R' and R" may be the same or different and each represents a hydrogen atom, an alkyl group or an aryl group.

Preferred examples of the cyanoheterocyclic compound will next be given. The alkyl group includes both linear and branched ones.

Preferred examples include 3-pyridyl cyanide, 2-methyl-3-pyridyl cyanide, 4-methyl-3-pyridyl cyanide, 5-methyl-3-pyridyl cyanide, 6-methyl-3-pyridyl cyanide, 2-ethyl-3-pyridyl cyanide, 4-ethyl-3-pyridyl cyanide, 5-ethyl-3-pyridyl cyanide, 6-ethyl-3-pyridyl cyanide, 2-propyl-3-pyridyl cyanide, 4-propyl-3-pyridyl cyanide, 5-propyl-3-pyridyl cyanide, 6-propyl-3-pyridyl cyanide, 2-butyl-3-pyridyl cyanide, 4-butyl-3-pyridyl cyanide, 5-butyl-3-pyridyl cyanide, 6-butyl-3-pyridyl cyanide, 2-phenyl-3-pyridyl cyanide, 4-phenyl-3-pyridyl cyanide, 5-phenyl-3-pyridyl cyanide, 6-phenyl-3-pyridyl cyanide, 2,4-dimethyl-3-pyridyl cyanide, 2,5-dimethyl-3-pyridyl cyanide, 2,6-dimethyl-3-pyridyl cyanide, 4,5-dimethyl-3-pyridyl cyanide, 4,6-dimethyl-3-pyridyl cyanide, 5,6-dimethyl-3-pyridyl cyanide, 2,4-diethyl-3-pyridyl cyanide, 2,5-diethyl-3-pyridyl cyanide, 2,6-diethyl-3-pyridyl cyanide, 4,5-diethyl-3-pyridyl cyanide, 4,6-diethyl-3-pyridyl cyanide, 5,6-diethyl-3-pyridyl cyanide, 2,4-dipropyl-3-pyridyl cyanide, 2,5-dipropyl-3-pyridyl cyanide, 2,6-dipropyl-3-pyridyl cyanide, 4,5-dipropyl-3-pyridyl cyanide, 4,6-dipropyl-3-pyridyl cyanide, 5,6-dipropyl-3-pyridyl cyanide, 2,4-dibutyl-3-pyridyl cyanide, 2,5-dibutyl-3-pyridyl cyanide, 2,6-dibutyl-3-pyridyl cyanide, 4,5-dibutyl-3-pyridyl cyanide, 4,6-dibutyl-3-pyridyl cyanide, 5,6-dibutyl-3-pyridyl cyanide, 2,4-diphenyl-3-pyridyl cyanide, 2,5-diphenyl-3-pyridyl cyanide, 2,6-diphenyl-3-pyridyl cyanide, 4,5-diphenyl-3-pyridyl cyanide, 4,6-diphenyl-3-pyridyl cyanide, 5,6-diphenyl-3-pyridyl cyanide, 4-pyridyl cyanide, 2-methyl-4-pyridyl cyanide, 3-methyl-4-pyridyl cyanide, 2-ethyl-4-pyridyl cyanide, 3-ethyl-4-pyridyl cyanide, 2-propyl-4-pyridyl cyanide, 3-propyl-4-pyridyl cyanide, 2-butyl-4-pyridyl cyanide, 3-butyl-4-pyridyl cyanide, 2-phenyl-4-pyridyl cyanide, 3-phenyl-4-pyridyl cyanide, 2,3-dimethyl-4-pyridyl cyanide, 2,5-dimethyl-4-pyridyl cyanide, 2,6-dimethyl-4-pyridyl cyanide, 3,5-dimethyl-4-pyridyl cyanide, 2,3-diethyl-4-pyridyl cyanide, 2,5-diethyl-4-pyridyl cyanide, 2,6-diethyl-4-pyridyl cyanide, 3,5-diethyl-4-pyridyl cyanide, 2,3-dipropyl-4-pyridyl cyanide, 2,5-dipropyl-4-pyridyl cyanide, 2,6-dipropyl-4-pyridyl cyanide, 3,5-dipropyl-4-pyridyl cyanide, 2,3-dibutyl-4-pyridyl cyanide, 2,5-dibutyl-4-pyridyl cyanide, 2,6-dibutyl-4-pyridyl cyanide, 3,5-dibutyl-4-pyridyl cyanide, 2,3-diphenyl-4-pyridyl cyanide, 2,5-diphenyl-4-pyridyl cyanide, 2,6-diphenyl-4-pyridyl cyanide, 3,5-diphenyl-4-pyridyl cyanide, 2,3,5-trimethyl-4-pyridyl cyanide, 2,3,6-trimethyl-4-pyridyl cyanide, 2,3,5-triethyl-4-pyridyl cyanide, 2,3,6-triethyl-4-pyridyl cyanide, 2,3,5-tripropyl-4-pyridyl cyanide, 2,3,6-tripropyl-4-pyridyl cyanide, 2,3,5-tributyl-4-pyridyl cyanide, 2,3,6-tributyl-4-pyridyl cyanide, 2,3,5-triphenyl-4-pyridyl cyanide, and 2,3,6-triphenyl-4-pyridyl cyanide.

Especially preferred are 3-pyridyl cyanide, 2-methyl-3-pyridyl cyanide, 4-methyl-3-pyridyl cyanide, 5-methyl-3-pyridyl cyanide, 6-methyl-3-pyridyl cyanide, 2,4-dimethyl-3-pyridyl cyanide, 2,5-dimethyl-3-pyridyl cyanide 2,6-dimethyl-3-pyridyl cyanide, 4,5-dimethyl-2-pyridyl cyanide, 4,6-dimethyl-3-pyridyl cyanide, 5,6-dimethyl-3-pyridyl cyanide, 4-pyridyl cyanide, 2-methyl-4-pyridyl cyanide, 3-methyl-4-pyridyl cyanide, 2-phenyl-3-pyridyl cyanide, 4-phenyl-3-pyridyl cyanide, 5-phenyl-3-pyridyl cyanide, 6-phenyl-3-pyridyl cyanide, 2-phenyl-4-pyridyl cyanide, 3-phenyl-4-pyridyl cyanide, 2,3-dimethyl-4-pyridyl cyanide, 2,5-dimethyl-4-pyridyl cyanide, 2,6-dimethyl-4-pyridyl cyanide and 3,5-dimethyl-4-pyridyl cyanide.

The above-exemplified cyanoheterocyclic compounds are easily commercially available. They are also available in a conventional manner by introducing various carboxylic acids into corresponding acid amides and then dehydrating the resulting acid amides, or introducing various aldehydes into corresponding aldoximes and then dehydrating the resulting aldoximes.

Step B

An amidrazone compound (III) is reacted with a diketone compound of the formula (IV) to obtain a 1,2,4-triazine compound of the formula (V). The 1,2,4-triazine compound (V) is available by the process as described in Japanese Patent Application No. Hei 11-167308 or Tetrahedron Lett., 39, 8817, 8821, 8825 (1998), or a process in accordance therewith.

Examples of the diketone compound of the formula (IV) include:

(i) Symmetric diketone compounds (in the case where X1 and X2 are the same and represent an alkyl or aryl group).

They are compounds of the formula (IV) wherein X1 and X2 are the same and represent an alkyl or aryl group. X1 and X2 may be coupled together to form a ring.

As the alkyl group, alkyl groups having 1 to 4 carbon atoms are preferred, while as the aryl group, phenyl and 4-methylphenyl groups are preferred. Specific examples include 1,2-cyclohexanedione, 2,3-butanedione, 3,4-hexanedione, 4,5-octanedione, 5,6-decanedione, 2,5-dimethyl-3,4-hexanedione, 2,7-dimethyl-4,5-octanedione, 3,6-dimethyl-4,5-octanedione, 2,2,5,5-tetramethyl-3,4-hexanedione, Benzyl, 4,4'-dimethylbenzyl, di-α-naphthylethanedione and di-β-naphthylethanedione. Particularly preferred are 1,2-cyclohexanedione, 2,3-butanedione, 3,4-hexanedione, Benzil and 4,4'-dimethylbenzyl.

(ii) Asymmetric diketone compounds (when X1 and X2 are different and each represents an alkyl or aryl group).

They are compounds represented by the formula (IV) wherein X1 and X2 are different and each represents an alkyl or aryl group. As the alkyl group, alkyl groups having 1 to 4 carbon atoms are preferred, while as the aryl group, phenyl and 4-methylphenyl groups are preferred.

Specific examples include 2,3-pentanedione, 2,3-hexanedione, 2,3-heptanedione, 4-methyl-2,3-pentanedione, 4-methyl-2,3-hexanedione, 5-methyl-2,3-hexanedione, 3,4-heptanedione, 3,4-octanedione, 2-methyl-3,4-hexanedione, 4,4-dimethyl-2,3-pentanedione, 5-methyl-3,4-heptanedione, 6-methyl-3,4-heptanedione, 2,2-dimethyl-3,4-hexanedione, 4,5-nonanedione, 3-methyl-4,5-octanedione, 2-methyl-4,5-octanedione, 2,2-dimethyl-3,4-heptanedione, 2-methyl-3,4-heptanedione, 2-methyl-3,4-octanedione, 2,5-dimethyl-3,4-heptanedione, 2,6-dimethyl-3,4-heptanedione, 2,2,5-trimethyl-3,4-hexanedione, 2-methyl-3,4-octanedione, 3-methyl-4,5-nonanedione, 2-methyl-4,5-nonanedione, 2,2-dimethyl-3,4-octanedione, 2,5-dimethyl-3,4-heptanedione, 2,6-dimethyl-4,5-octanedione, 2,2, 5-trimethyl-heptanedione, 2,5-dimethyl-3,4-hexanedione, 2,6-dimethyl-4,5-octanedione, 2,2,6-trimethyl-3,4-heptanedione, 2,2,6-trimethyl-3,4-hexanedione, 2,2-5-trimethyl-3,4-heptanedione, 2,2,6-trimethyl-3,4-heptanedione, 1-phenyl-1,2-propanedione, 1-phenyl-1,2-butanedione, 1-phenyl-1,2-heptanedione, 3-methyl-1-phenyl-1,2-butanedione, 1-phenyl-1,2-hexanedione, 3-methyl-1-phenyl-1,2-heptanedione, 4-methyl-l-phenyl-1,2-heptanedione and 3,3-dimethyl-1-phenyl-1,2-butanedione.

Particularly preferred are 2,3-pentanedione, 2,3-heptanedione and 1-phenyl-1,2-propanedione.

(iii) Dialdehyde compounds (having a hydrogen atom as each of X1 and X2).

Specific examples include an aqueous glyoxal solution, glyoxal di(sodium bisulfite), and 1,4-dioxane-2,3-diol and glyoxal trimeric dihydrate which are glyoxal equivalents, of which an aqueous glyoxal solution and 1,4-dioxane-2,3-diol are preferred, with an aqueous glyoxal solution being more preferred because of its availability at a low cost and handing ease.

(iv) Ketoaldehyde compounds (having a hydrogen atom as one of X1 and X2 and an alkyl group as the other one).

They are compounds of the formula (IV) wherein one of X1 and X2 represents a hydrogen atom and the other one represents an alkyl or aryl group. Preferred are the compounds wherein the alkyl group is an alkyl group having 1 to 4 carbon atoms or the aryl group is a phenyl group. Specific examples include methylglyoxal (pyruvic aldehyde), ethylglyoxal, propylglyoxal, isopropylglyoxal, butylglyoxal, t-butylglyoxal, isobutylglyoxal, sec-butylglyoxal and phenylglyoxal. Of these, methylglyoxal and phenylglyoxal are especially preferred.

The 1,2,4-triazine compound of the formula (V) is also available by the process as described in Tetrahedron Lett., 25, 2315(1971) or Tetrahedron, 33, 1043(1977) which uses an acid hydrazide and α-haloketone, or a process in accordance therewith.

Step C

The 1,2,4-triazine compound of the formula (V) is reacted with 2,5-norbornadiene to obtain a pyridine derivative of the formula (I). The pyridine derivative of the formula (I) is available by the process as described in Tetrahedron Lett., 39, 8817, 8821, 8825 (1988) or a process in accordance therewith.

BEST MODE FOR CARRYING OUT THE INVENTION

The present invention will hereinafter be described in further detail by Examples. It should however be borne in mind that the invention is not limited to or by them. The purity was evaluated based on high-performance liquid chromatography (which will be abbreviated as "HPLC").

EXAMPLE 1

Synthesis of 3-(5,6-Diphenyl-2-pyridyl)pyridine (A-4)

In a 50-mL egg-plant flask, 1.0 ml of water, 0.99 g (9.5 mmole) of 3-cyanopyridine and 5.5 g (0.095 mole) of a hydrazine monohydrate were charged and they were reacted at 30° C. for 3 hours under stirring. After disappearance of raw materials was confirmed by HPLC analysis, 10 ml of toluene was added and from the resulting mixture, water and excess hydrazine were distilled off under reduced pressure. This operation was repeated three times in total. To the residue were added 5.5 ml of water and 5.5 ml of ethanol, followed by the addition of 2.0 g (9.5 mmole) of Benzil. The mixture was reacted for 2 hours at an external temperature of 100° C. To the reaction mixture was added 10 ml of toluene and the solvent was distilled off under reduced pressure. In 10 ml of xylene, 8.8 g (0.095 mole) of 2,5-norbornadiene was dissolved. The resulting solution was added to the residue, followed by reaction for 24 hours under reflux. After completion of the reaction, xylene and excess 2,5-norbornadiene were distilled off under reduced pressure. To the residue was added 10 ml of toluene and 2,5-norbornadiene was completely distilled off. The residue was purified by chromatography on a silica gel column, followed by recrystallization from hexane, whereby 1.8 g (yield: 63.2%) of the target compound was obtained as pale yellow crystals. The product was found to have a purity of 99.3%.

EXAMPLES 2 TO 27

In a similar manner to that employed for Example 1, Compounds A-1 to A-3, A-5 to A-27 were synthesized. Their structure and properties are shown below in Tables 1 to 6.

TABLE 1

| Compound No. (Appearance and form) | Yield/purity (%) Melting point (° C.) MS (FAB) | 1H-NMR (CDCl₃) |
|---|---|---|
| 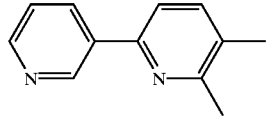<br>A-1<br>(Brown viscose oil) | 56.2/99.3<br>—<br>185 (M + 1)⁺ | 2.33(s, 3H)<br>2.58(s, 3H)<br>7.37(dd, J=4.9, 2.9Hz, 1H)<br>7.49(s, 2H)<br>8.29–8.32(m, 1H)<br>8.60(dd, J=3.3, 1.4Hz, 1H)<br>9.16(d, J=1.7Hz, 1H) |
| 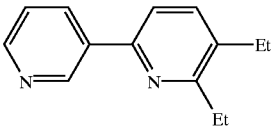<br>A-2<br>(Pale yellow viscous oil) | 54.0/99.0<br>—<br>213 (M + 1)⁺ | 1.26(t, J=7.6Hz, 3H)<br>1.37(t, J=7.4Hz, 3H)<br>2.70(q, J=7.5Hz, 2H)<br>2.90(q, J=7.5Hz, 2H)<br>7.36–7.39(m, 1H)<br>7.53(s, 1H)<br>8.34–8.37(m, 1H)<br>8.60(dd, J=3.1, 1.7Hz, 1H)<br>9.21(d, J=7.1Hz, 1H) |
| 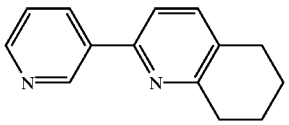<br>A-3<br>(Brown viscous oil) | 60.7/99.2<br>—<br>211 (M + 1)⁺ | 1.82–1.88(m, 2H)<br>1.91–1.97(m, 2H)<br>2.82(t, J=6.3Hz, 2H)<br>3.00(t, J=6.4Hz, 2H)<br>7.37(dd, J=4.8H, 3.1Hz, 1H)<br>7.46(dd, J=8.1, 2.8Hz, 2H)<br>8.27–8.30(m, 1H)<br>8.61(dd, J=3.3, 1.5Hz, 1H)<br>9.14(d, J=2.0Hz, 1H) |
| 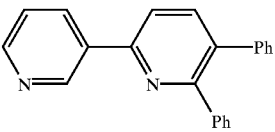<br>A-4<br>(Yellow crystals) | 45.6/99.3<br>204 to 205<br>309 (M + 1)⁺ | 7.17–7.21(m, 3H)<br>7.27–7.36(m, 10H)<br>7.67–7.69(m, 1H)<br>8.50(dd, J=3.2, 1.6Hz, 1H)<br>8.71(d, J=1.6Hz, 1H) |
| 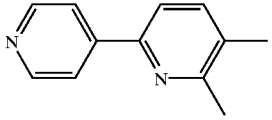<br>A-5<br>(Pale yellow crystals) | 50.1/99.2<br>66 to 68<br>185 (M + 1)⁺ | 2.34(s, 3H)<br>2.59(s, 3H)<br>7.64(t, J=7.2Hz, 2H)<br>7.89(dd, J=2.8, 1.7Hz, 2H)<br>8.68(dd, J=2.9, 1.6Hz, 2H) |

TABLE 2

| Compound No. (Appearance and form) | Yield/purity (%) Melting point (° C.) MS (FAB) | 1H-NMR (CDCl₃) |
|---|---|---|
| 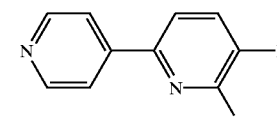<br>A-6<br>(Brown viscous oil) | 49.4/98.8<br>—<br>213 (M + 1)⁺ | 1.26(t, J=7.5Hz, 3H)<br>1.38(t, J=7.5Hz, 3H)<br>2.71(q, J=7.5Hz, 2H)<br>2.91(q, J=7.5Hz, 2H)<br>7.56(dd, J=9.8, 7.9Hz, 2H)<br>7.93(dd, J=3.3, 1.4Hz, 2H)<br>8.68(t, J=3.0Hz, 2H) |
| 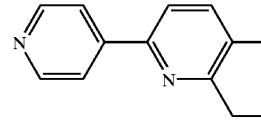<br>A-7<br>(Pale yellow viscous oil) | 60.9/99.3<br>—<br>211 (M + 1)⁺ | 1.83–1.88(m, 2H)<br>1.91–1.97(m, 2H)<br>2.82(t, J=6.2Hz, 2H)<br>3.00(t, J=6.3Hz, 2H)<br>7.46(d, J=7.9Hz, 1H)<br>7.52(d, J=7.9Hz, 1H)<br>7.86(dd, J=3.0, 1.6Hz, 2H)<br>8.68(dd, J=3.0, 1.6Hz, 2H) |

TABLE 2-continued

| Compound No.<br>(Appearance and form) | Yield/purity (%)<br>Melting point (° C.)<br>MS (FAB) | 1H-NMR<br>(CDCl₃) |
|---|---|---|
| 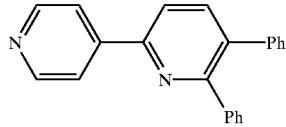<br>A-8<br>(Yellow crystals) | 58.1/99.3<br>145 to 148<br>309 (M + 1)⁺ | 7.21–7.31(m, 8H)<br>7.45–7.49(m, 2H)<br>7.85(s, 2H)<br>8.04(dd, J=2.9, 1.6Hz, 2H)<br>8.74(dd, J=3.0, 1.6Hz, 2H) |
| 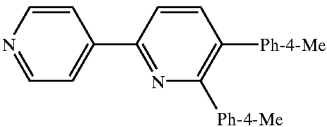<br>A-9<br>(Pale yellow crystals) | 53.7/99.0<br>148 to 151<br>337 (M + 1)⁺ | 2.34(s, 3H)<br>2.36(s, 3H)<br>7.12(s, 6H)<br>7.38(d, J=8.1Hz, 2H)<br>7.81(s, 2H)<br>8.04(dd, J=3.0, 1.5Hz, 2H) |
| 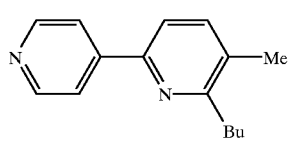<br>A-10<br>(Pale yellow crystals) | 22.8/98.8<br>69 to 70<br>227 (M + 1)⁺ | 0.99(t, J=7.3Hz, 2H)<br>1.44–1.51(m, 2H)<br>1.74–2.05(m, 2H)<br>2.36(s, 3H)<br>2.85(t, J=7.8Hz, 3H)<br>7.52(dd, J=7.9, 6.1Hz, 2H)<br>7.91(d, J=5.5Hz, 2H)<br>8.68(s, 2H) |

TABLE 3

| Compound No.<br>(Appearance and form) | Yield/purity (%)<br>Melting point (° C.)<br>MS (FAB) | 1H-NMR<br>(CDCl₃) |
|---|---|---|
| 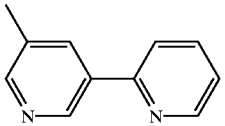<br>A-11<br>(Pale yellow oil) | 83.5/99.2<br>—<br>171 (M + 1)⁺ | 2.43(s, 3H)<br>7.29(t, J=3.6Hz, 1H)<br>7.74–7.79(m, 2H)<br>8.16(s, 1H)<br>8.49(s, 1H)<br>8.72(t, J=2.4Hz, 1H)<br>8.97(s, 1H) |
| 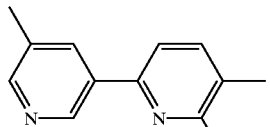<br>A-12<br>(Pale yellow oil) | 55.6/99.0<br>—<br>199 (M + 1)⁺ | 2.33(s, 3H)<br>2.42(s, 3H)<br>2.58(s, 3H)<br>7.47(d, J=8.0Hz, 2H)<br>8.14(s, 1H)<br>8.44(s, 1H)<br>8.93(s, 1H) |
| 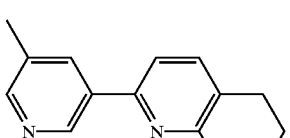<br>A-13<br>(Pale yellow oil) | 49.8/98.9<br>—<br>225 (M + 1)⁺ | 1.83–1.87(m, 2H)<br>1.93–1.95(m, 2H)<br>2.41(s, 3H)<br>2.82(t, J=6.4Hz, 2H)<br>7.45(d, J=2.8Hz, 2H)<br>8.11(t, J=1.3Hz, 1H)<br>8.44(d, J=1.7Hz, 1H)<br>8.92(d, J=1.0Hz, 1H) |

TABLE 3-continued

| Compound No. (Appearance and form) | Yield/purity (%) Melting point (° C.) MS (FAB) | 1H-NMR (CDCl₃) |
|---|---|---|
| 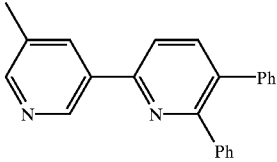<br>A-14<br>(Pale yellow crystals) | 49.8/99.1<br>240 (decomp.)<br>323 (M + 1)⁺ | 2.44(s, 3H)<br>7.12–7.30(m, 7H)<br>7.47(dd, J=4.0, 2.8Hz, 3H)<br>7.81(dd, J=7.9, 4.9Hz, 2H)<br>8.31(s, 1H)<br>8.49(s, 1H)<br>9.10(s, 1H) |
| 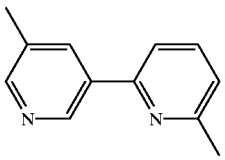<br>A-15<br>(Pale yellow oil) | 44.5/99.3<br>—<br>185 (M + 1)⁺ | 2.42(s, 3H)<br>2.64(s, 3H)<br>7.15(d, J=7.7Hz, 1H)<br>7.53(d, J=7.8Hz, 1H)<br>7.67(t, J=7.7Hz, 1H)<br>8.15(s, 1H)<br>8.47(s, 1H)<br>8.95(s, 1H) |

TABLE 4

| Compound No. (Appearance and form) | Yield/purity (%) Melting point (° C.) MS (FAB) | 1H-NMR (CDCl₃) |
|---|---|---|
| 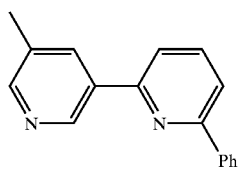<br>A-16<br>(Pale yellow crystals) | 43.2/99.2<br>82 to 83<br>247 (M + 1)⁺ | 2.46(s, 3H)<br>7.46(d, J=7.2Hz, 1H)<br>7.52(t, J=7.5Hz, 2H)<br>7.73(dd, J=7.8, 5.6Hz, 2H)<br>7.86(t, J=7.8Hz, 1H)<br>8.14(t, J=4.4Hz, 2H)<br>8.30(s, 1H)<br>8.50(s, 1H)<br>9.11(s, 1H) |
| 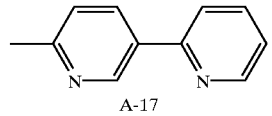<br>A-17<br>(Pale yellow oil) | 82.9/99.3<br>—<br>171 (M + 1)⁺ | 2.27(s, 3H)<br>7.25–7.28(m, 2H)<br>7.71–7.80(m, 2H)<br>8.22(dd, J=5.8, 2.4Hz, 1H)<br>8.70(dd, J=3.9, 1.0Hz, 1H)<br>9.06(d, J=2.2Hz, 1H) |
| 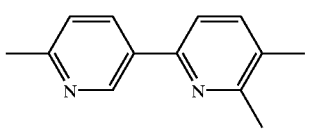<br>A-18<br>(Pale yellow cyrstals) | 60.1/99.2<br>75 to 77<br>199 (M + 1)⁺ | 2.32(s, 3H)<br>2.57(s, 3H)<br>2.60(s, 3H)<br>7.23(d, J=8.1Hz, 1H)<br>7.47(d, J=2.3Hz, 2H)<br>8.21(dd, J=5.8, 2.3Hz, 1H)<br>9.02(d, J=2.0Hz, 1H) |
| 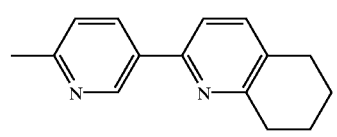<br>A-19<br>(Pale yellow oil) | 56.8/99.1<br>—<br>225 (M + 1)⁺ | 1.83–1.92(m, 2H)<br>1.94–1.96(m, 2H)<br>2.60(s, 3H)<br>2.81(t, J=6.2Hz, 2H)<br>2.99(t, J=6.4Hz, 2H)<br>7.23(d, J=8.1Hz, 2H)<br>7.43(t, J=8.2Hz, 1H)<br>8.19(dd, J=5.8, 2.3Hz, 1H)<br>9.01(d, J=2.2Hz, 1H) |

TABLE 4-continued

| Compound No. (Appearance and form) | Yield/purity (%) Melting point (° C.) MS (FAB) | 1H-NMR (CDCl₃) |
|---|---|---|
| 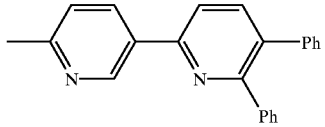 A-20 (Pale yellow cyrstals) | 41.2/98.8 114 to 115 323 (M + 1)⁺ | 2.69(s, 3H) 7.21–7.77(m, 11H) 7.81(t, J=7.4Hz, 2H) 8.40(dd, J=5.8, 2.3Hz, 1H) 9.19(d, J=2.0Hz, 1H) |

TABLE 5

| Compound No. (Appearance and form) | Yield/purity (%) Melting point (° C.) MS (FAB) | 1H-NMR (CDCl₃) |
|---|---|---|
| 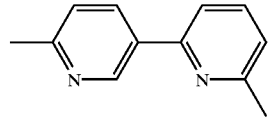 A-21 (Pale yellow oil) | 39.8/99.0 — 185 (M + 1)⁺ | 2.61(s, 3H) 2.63(s, 3H) 7.13(d, J=7.6Hz, 1H) 7.24(s, 1H) 7.51(d, J=7.8Hz, 1H) 7.66(t, J=7.7Hz, 1H) 8.23(dd, J=5.8, 2.2Hz, 1H) 9.03(d, J=1.8Hz, 1H) |
| 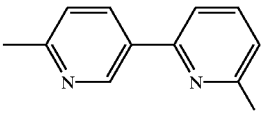 A-22 (Brown oil) | 41.2/98.9 — 247 (M + 1)⁺ | 2.65(s, 3H) 7.30(d, J=8.1Hz, 1H) 7.45(t, J=4.2Hz, 1H) 7.51(dd, J=5.5, 4.6Hz, 2H) 7.71(dd, J=7.7, 4.8Hz, 2H) 7.84(t, J=7.8Hz, 1H) 8.14(t, J=5.0Hz, 2H) 8.41(dd, J=5.8, 2.3Hz, 1H) 9.21(d, J=2.0Hz, 1H) |
| 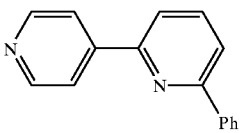 A-23 (Pale yellow oil) | 43.2/99.0 — 233 (M + 1)⁺ | 7.47–7.52(m, 3H) 7.79(dd, J=7.5, 7.0Hz, 2H) 7.89(d, J=7.8Hz, 1H) 8.06(t, J=3.1Hz, 2H) 8.15(t, J=4.3Hz, 2H) 8.75(d, J=5.8Hz, 2H) |
| 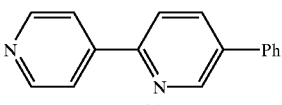 A-24 (Pale yellow oil) | 40.5/99.0 — 233 (M + 1)⁺ | 7.52(t, J=7.4Hz, 2H) 7.64(d, J=7.1Hz, 2H) 7.76–7.88(m, 1H) 7.93(d, J=5.8Hz, 1H) 8.04(d, J=5.9Hz, 1H) 8.15(d, J=8.2Hz, 1H) 8.31(d, J=7.6Hz, 1H) 8.51(d, J=5.8, 1H) 8.75(d, J=4.1Hz, 1H) 8.87(d, J=5.4Hz, 1H) |
| 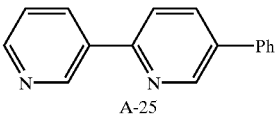 A-25 (Pale yellow oil) | 37.8/99.1 — 233 (M + 1)⁺ | 7.21(d, J=2.4Hz, 3H) 7.49–7.52(m, 2H) 7.78(d, J=4.5Hz, 1H) 7.92–7.95(m, 3H) 8.28(s, 2H) |

TABLE 6
| Compound No. (Appearance and form) | Yield/purity (%) Melting point (° C.) MS (FAB) | 1H-NMR (CDCl₃) |
|---|---|---|
| 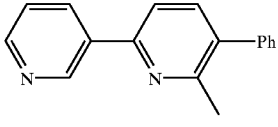 A-26 (Pale yellow oil) | 33.5/99.0 — 247 (M + 1)⁺ | 2.62(s, 3H) 7.34(t, J=3.8Hz, 1H) 7.43–7.52(m, 6H) 7.70(t, J=4.5Hz, 1H) 7.74(d, J=7.3Hz, 1H) 8.07–8.10(m, 2H) |
| 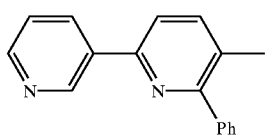 A-27 (Pale yellow oil) | 31.4/89.9 — 247 (M + 1)⁺ | 2.43(s, 3H) 7.36–7.51(m, 5H) 7.62–7.67(m, 4H) 8.42(dd, J=4.5, 1.8Hz, 1H) 9.24(s, 1H) |
EXAMPLES 28 TO 44
Compounds A-28 to A-44 having the below-described structure were synthesized in a manner similar to that employed for Example 1 and were identified as described above.
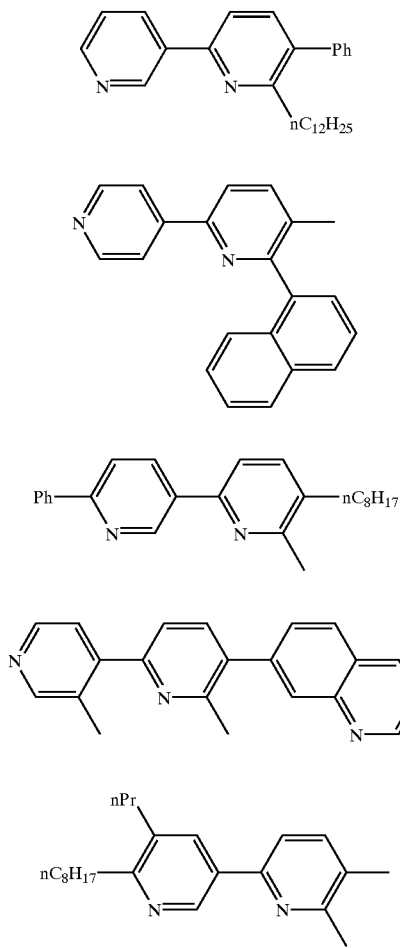
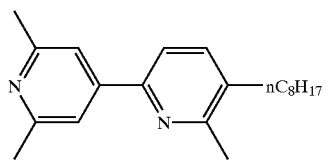
(A-33)
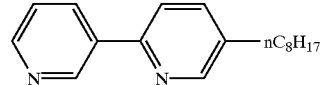
(A-34)
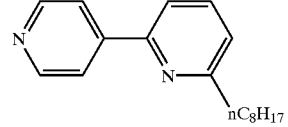
(A-35)
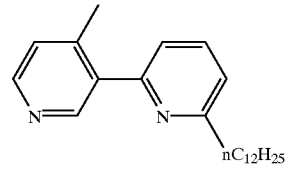
(A-36)
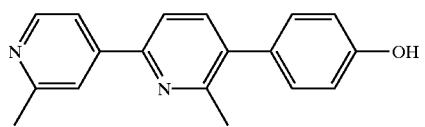
(A-37)
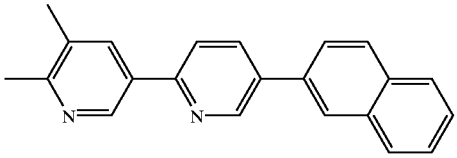
(A-38)
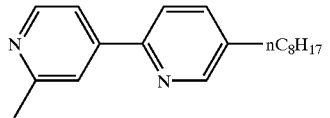
(A-39)

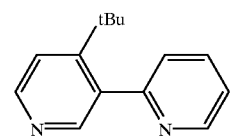
(A-40)

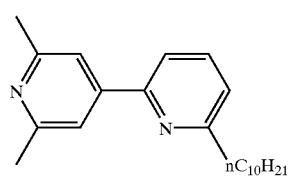
(A-41)

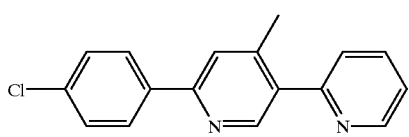
(A-42)

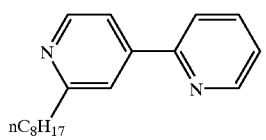
(A-43)

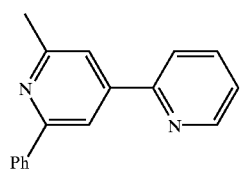
(A-44)

APPLICATION EXAMPLES

The following are some application examples of the novel pyridine derivative of the invention. It should however be borne in mind that the present invention is not limited to or by it at all.

In this application example, the compound was used as a co-catalyst (ligand) of a metal copper catalyst in the Ullmann-type reaction as described in Japanese Patent Laid-Open No. Hei 11-130738 or Japanese Patent Laid-Open No. Hei 11-199549. As a substrate, the following substance was employed.

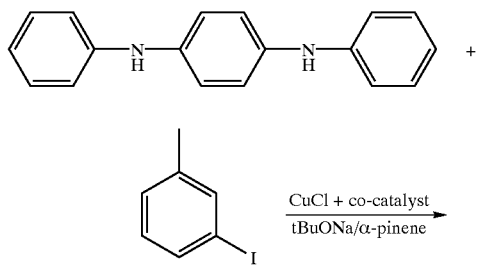

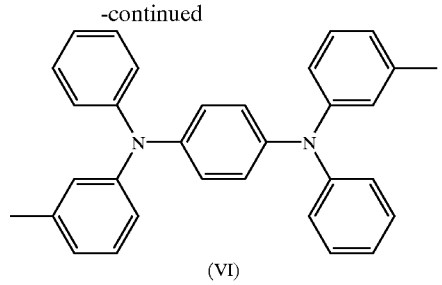
(VI)

Application Example 1

Synthesis of N,N'-Diphenyl-N,N'-di(3-methylphenyl)-1,4-phenylenediamine (VI)

A mixture of 31.2 g (0.12 mole) of N,N'-diphenyl-N,N'-p-phenylenediamine, 54.5 g (0.25 mole) of m-iodotoluene, 32.6 g (0.34 mole) of t-butoxy sodium, 59.0 mg (0.6 mmole) of copper (I) chloride, 185 mg (0.6 mmole) of 2-(5,6-diphenyl-2-pyridyl)pyridine (A-8) and 87.6 ml of α-pinene was reacted at 125 to 130° C. for 5 hours under a nitrogen gas stream. After completion of the reaction, 66 ml of toluene and 66 ml of water were added to separate the reaction mixture. Toluene was then concentrated under reduced pressure. The residue was crystallized by the addition of 39 ml of ethyl acetate and 253 ml of isopropanol, whereby 47.8 g (yield: 90.5%) of the target compound was obtained as pale yellow crude crystals. The compound was found to have a melting point of 170 to 171° C. and an HPLC content (column: YMC-A-002, UV detector: 310 nm, eluent having a flow rate of 1.1 ml/min) was 99.5%.

Application Examples 2 to 4

In a similar manner to Application Example 1 except that a co-catalyst as shown below in Table 2 was used instead of 2-(5,6-diphenyl-2-pyridyl)pyridine (A-8), N,N'-diphenyl-N,N'-di(3-methylphenyl)-1,4-phenylenediamine was synthesized and its purity based on HPLC was evaluated as well as its yield.

Comparative Examples 1 to 6

In a similar manner to Example 1 except that a co-catalyst as shown below in Table 6 was used instead of 2-(5,6-diphenyl-2-pyridyl)pyridine (A-8), N,N'-diphenyl-N,N'-di(3-methylphenyl)-1,4-phenylenediamine was synthesized and its accelerating effect based on the reaction time, its yield, and its purity based on HPLC were evaluated. In Application Examples and Comparative Examples 3 to 6, the time point when no progress of the reaction was recognized was designated as the terminal point of the reaction and evaluation was conducted at this point.

The results are shown in Table 7.

TABLE 7

|  | Co-catalyst | Reaction time (hr) | HPLC content (%) | Yield (%) |
|---|---|---|---|---|
| Application Example 1 | A-8 | 3 | 99.5 | 90.5 |
| Application Example 2 | A-5 | 5 | 99.5 | 89.9 |

TABLE 7-continued

|  | Co-catalyst | Reaction time (hr) | HPLC content (%) | Yield (%) |
|---|---|---|---|---|
| Application Example 3 | A-3 | 5 | 99.4 | 88.5 |
| Application Example 4 | A-16 | 4 | 99.3 | 89.2 |
| Comparative Example 1 | Free | 3 | 45.5 | 12.4 |
| Comparative Example 2 | Free | 5 | 73.2 | 24.1 |
| Comparative Example 3 | Free | 13 | 99.1 | 63.1 |
| Comparative Example 4 | Pyridine | 15 | 99.2 | 77.8 |
| Comparative Example 5 | 2-Phenylpyridine | 15 | 99.2 | 66.0 |
| Comparative Example 6 | 2,4'-dipyridyl | 9 | 99.3 | 80.4 |

As is apparent from Table 7, the reaction was markedly accelerated and the target compound having a higher purity was obtained in a higher yield when the dipyridyl derivative of the invention was added as a co-catalyst (ligand) compared with the conventional reaction using only a copper catalyst, or with reaction using a co-catalyst such as pyridine, 2-phenylpyridine or 2,4'-dipyridyl. When the reaction is terminated prior to the complete consumption of the raw materials as in Comparative Example 1 or 2, the purity of the compound lowers extremely owing to difficulty in purification. This also applies to the case wherein the co-catalysts used in Comparative Examples 4 to 6 were added.

These novel dipyridyl derivatives can be applied to a photographic halogenated emulsion such as a nucleating accelerator or crystal habit modifier as described in Japanese Patent Laid-Open No. Hei 6-242534 or Japanese Patent Laid-Open No. Hei 8-227117 by introducing them, as an intermediate, into Compounds B-1 to B-5 having the below-described structures, and are therefore very useful from the industrial viewpoint.

The synthesizing process of them will next be described.

Application Example 5

Synthesis of 1-benzyl-4-(5-methyl-6-(α-naphthyl)-2-pyridyl)pyridinium chloride (B-1).

Benzyl chloride (0.82 g, 6.5 mmole) was added dropwise to 1.6 g (5.4 mmole) of 3-methyl-2-(α-naphthyl)-6-(4-pyridyl)pyridine and 5 ml of isopropyl alcohol, followed by heating under reflux for 3 hours. After completion of the reaction, 12 ml of ethyl acetate was added. After cooling to 10° C., the mixture was filtered, whereby 2.2 g (yield: 96.5%) of the target product was obtained. By the 1H-NMR, MS, IR and elemental analysis, it was confirmed to be the target product.

Application Examples 6 to 10

In a similar and corresponding manner to Application Example 5, Compounds B-1 to B-5 having the below-described structures were synthesized. They were identified by the 1H-NMR, MS, IR and elemental analysis.

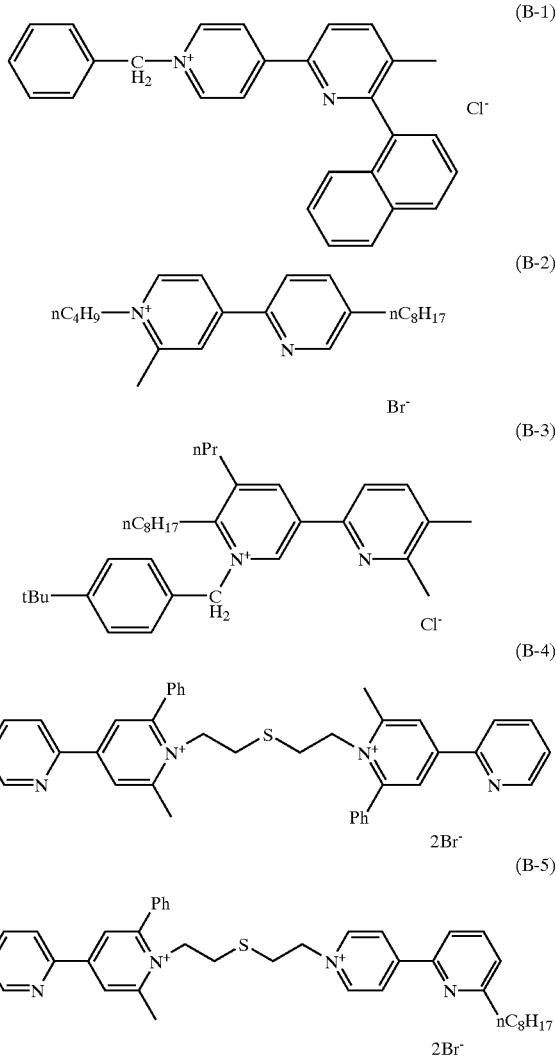

Industrial Applicability

According to the present invention, dipyridyl derivatives are provided as a novel compound. This invention makes it possible to expand the acquisition route of pharmaceuticals, agrichemicals, ligands, silver halide photosensitive materials, liquid crystals, surfactants, electrophotography and organic electroluminescence having a novel pyridine nucleus. The present invention has therefore a significant meaning in the research and development, or industrialization or practical use in these fields.

What is claimed is:

1. A dipyridyl compound represented by the following formula (A):

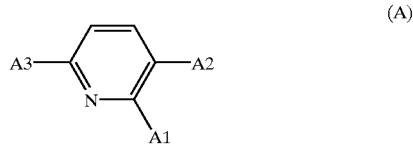

wherein A1 and A2 may be the same or different and each represents an alkyl group; A1 and A2 may be coupled together to form a ring; and A3 represents one of the following structures:

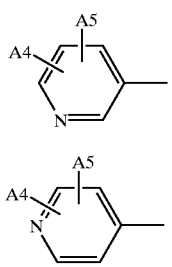

(AI)

(AII)

wherein A4 and A5 may be the same or different and each represents a hydrogen atom, an alkyl group or an aryl group.

2. A dipyridyl compound according to claim 1, wherein in A1, A2, A4 or A5 of the formula (A), the alkyl group has 1 to 4 carbon atoms.

3. A dipyridyl compound according to claim 2, wherein in the formula (A), A1 and A2 are the same.

4. A dipyridyl compound represented by the following formula (B):

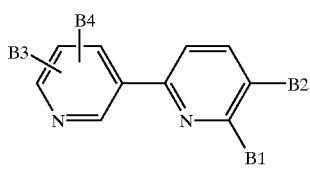

(B)

wherein one of B1 and B2 represents a hydrogen atom, and the other represents an alkyl or aryl group, and B3 and B4 may be the same or different and each represents a hydrogen atom, an alkyl group or an aryl group, with the proviso that when B3 and B4 simultaneously represent a hydrogen atom, the following cases are excluded:
(i) one of B1 and B2 represents an alkyl group having 3 or less carbon atoms, and (ii) B1 represents a phenyl group, and with the further proviso that when B2 represents a hydrogen atom, the following case are excluded:
(i) each of B 1 and B3 (substituted at the 6-position) represents a phenyl group and B4 represents a hydrogen atom, or
(ii) B 1, B3 (substituted at the 2-position) and B4 (substituted at the 6-position) each represents a methyl group.

5. A dipyridyl compound according to claim 4, wherein in B1, B2, B3 or B4 of the formula (B), the alkyl group has 1 to 4 carbon atoms and the aryl group is a phenyl or naphthyl group.

6. A dipyridyl compound represented by the following formula (C):

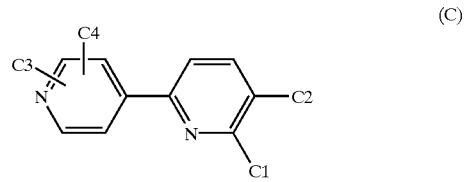

(C)

wherein one of C1 and C2 represents a hydrogen atom and the other one represents an alkyl or aryl group; and C3 and C4 may be the same or different and each represents a hydrogen atom, an alkyl group or an aryl group, with the proviso that when C3 and C4 simultaneously represent a hydrogen atom, C1 or C2 does not represent a methyl group.

7. A dipyridyl compound according to claim 6, wherein in C1, C2, C3 or C4 of the formula (C), the alkyl group has 1 to 4 carbon atoms and the aryl group is a phenyl or naphthyl group.

* * * * *